(12) United States Patent
Flach et al.

(10) Patent No.: US 8,386,057 B2
(45) Date of Patent: Feb. 26, 2013

(54) ELECTRODE CATHETER FOR INTERVENTIONAL USE

(75) Inventors: Erhard Flach, Berlin (DE); Wolfgang Geistert, Rheinfelden (DE); Michelle Maxfield, Berlin (DE); Ingo Weiss, Berlin (DE); Michael Friedrich, Kleinmachnow (DE)

(73) Assignee: Biotronik CRM Patent AG, Baar (CH)

( * ) Notice: Subject to any disclaimer, the term of this patent is extended or adjusted under 35 U.S.C. 154(b) by 1405 days.

(21) Appl. No.: 11/940,869

(22) Filed: Nov. 15, 2007

(65) Prior Publication Data

US 2012/0277840 A1 Nov. 1, 2012

(30) Foreign Application Priority Data

Nov. 17, 2006 (DE) .......................... 10 2006 054 620
May 12, 2007 (DE) .......................... 10 2007 022 333

(51) Int. Cl.
*A61N 1/05* (2006.01)
(52) U.S. Cl. ........................................ 607/119; 607/116
(58) Field of Classification Search ........... 607/116–138
See application file for complete search history.

(56) References Cited

U.S. PATENT DOCUMENTS

| | | | |
|---|---|---|---|
| 6,944,489 B2 | 9/2005 | Zeijlemaker et al. | |
| 7,551,967 B1 * | 6/2009 | Karicherla et al. | 607/122 |
| 2002/0043654 A1 * | 4/2002 | Karttunen et al. | 252/500 |
| 2003/0144720 A1 | 7/2003 | Villaseca | |
| 2003/0144721 A1 | 7/2003 | Villaseca | |
| 2004/0068313 A1 | 4/2004 | Jenney et al. | |
| 2005/0022658 A1 | 2/2005 | Bateman | |
| 2005/0288751 A1 | 12/2005 | Gray | |
| 2005/0288752 A1 | 12/2005 | Gray | |
| 2005/0288754 A1 | 12/2005 | Gray | |
| 2005/0288756 A1 | 12/2005 | Gray | |
| 2006/0009819 A1 | 1/2006 | Przybyszewski | |
| 2006/0200218 A1 | 9/2006 | Wahlstrand | |

FOREIGN PATENT DOCUMENTS

| | | |
|---|---|---|
| EP | 0884024 | 6/1997 |
| WO | 2004/095385 | 11/2004 |

OTHER PUBLICATIONS

Bonmassar, G.:Resistive Tapered Stripline (RTS) in Electroencephalogram Recordings During MRI.In:IEEE Transactions on Microwave Theory and Techniques, vol. 52, No. 8, Aug. 2004.
German Search Report, dated Aug. 13, 2007.
German Search Report, dated Feb. 20, 2008.
European Search Report date Sep. 16, 2009, 6 pages.

* cited by examiner

*Primary Examiner* — Carl H Layno
*Assistant Examiner* — Paula J Stice
(74) *Attorney, Agent, or Firm* — ARC IP Law, PC; Joseph J. Mayo (57) ABSTRACT

An electrode for interventional purposes, such as a cardiac pacemaker, neurostimulation, or ICD electrode, comprises an elongate electrode body (6), at least one electrode pole (5) in the area of the distal end (4) of the electrode body (6) for delivering an intervention pulse, at least one supply line (7) running in the electrode body (6) to the at least one electrode pole (5), and an electrode sheath (8) for insulating the supply line (7). The first and/or second material is produced in such a way that it contains conductive particles embedded in a polymer matrix in a concentration which is greater than or equal to the percolation threshold.

24 Claims, 11 Drawing Sheets

ELECTRODE CATHETER FOR INTERVENTIONAL USE

This application takes priority from German Patent Application DE 10 2006 054 620.2 filed 17 Nov. 2006 and German Patent Application DE 10 2007 022 333.3, filed 12 May 2007, the specifications of which are hereby incorporated herein by reference.

BACKGROUND OF THE INVENTION

1. Field of the Invention

The present invention relates to an electrode for interventional purposes, such as a pacemaker or ICD electrode or an electrophysiological catheter, as is used, for example, with pacemakers, defibrillators, neurostimulators, and in procedures of electrophysiology (EP).

2. Description of the Related Art

Electrodes of this type are known to have an elongate electrode body having a distal end and a proximal end. At least one active electrode pole for delivering an intervention pulse is provided in the area of the distal end. This electrode pole is designed, for example, as a tip electrode pole situated directly at the distal end, as a ring pole placed at a distance therefrom, or as a shock electrode. The intervention pulses delivered via this pole are, for example, the pacemaker pulses of a cardiac pacemaker and/or neurostimulator, a high-voltage pulse in the case of a defibrillator, or an ablation energy pulse in the case of an ablation device.

A supply line comprising a first material, which produces a connection to this electrode pole, runs in the electrode body. Furthermore, such electrodes for interventional purposes usually have further electrode poles to thus be referred to, using which the electrode may come into contact with tissue. A ring electrode pole of a bipolar electrode or an EP catheter are cited as examples. Furthermore, an electrode sheath which encloses the at least one supply line is provided in the electrode body, which comprises a second material. This material is usually insulating and/or different from the first material.

In recent years, magnetic resonance (MR) diagnostic devices, also referred to in the following as MR devices (such as magnetic resonance tomographs=MRT) have gained great significance because of their examination methods, which are protective of patients, noninvasive, and completely free of pain and side effects. Typical electrodes for interventional purposes display the problem that electrodes of this type heat up strongly in magnetic resonance diagnostic devices under the influence of the electromagnetic radiation thus generated because of electromagnetic induction and the discharge of the induced energy in the area of their contact surface(s) to the tissue. The reason for this is particularly the solid, metallic supply lines to the electrode poles, which act as an antenna and in which, because of their insulation, the antenna currents induced by high frequency (HF) fields may only be discharged into the body electrolytes at the electrode poles, which form the electrical interface to the tissue. The cited HF fields operate, for example, in an operating frequency range of 21 MHz in a 0.5 Tesla MR tomograph. The operating frequency range may extend up to 300 MHz in 7 Tesla MR tomographs according to the current prior art and is typically at 64 MHz in a 1.5 Tesla MR tomograph, for example. Because extremely strong heating in the tissue may occur in proximity to the electrode pole, access to magnetic resonance diagnostic devices is typically blocked to wearers of cardiological and neurological intervention devices, such as cardiac pacemakers, neurostimulators, or defibrillators.

To prevent and/or minimize the hazardous heating of the body cells, the maximum antenna current must be limited and/or reduced. Known solutions suggest discrete components for this purpose, which act as a band-stop filter or as a low-pass filter and thus limit the conduction resistance of the antenna for the frequencies of interest. Other solutions suggest capacitors, which are connected in parallel to the insulation and thus dissipate the antenna current.

In this regard, for example, U.S. Pat. No. 6,944,489, US 2003/0144720 A1, US 2003/0144721 A1, US 2005/0288751 A1 (and the simultaneously published parallel publications US 2005/0288752 A1, US 2005/0288754 A1, and US 2005/0288756 A1, which have essentially the same wording) are cited.

In principle, this possibility exists, of influencing the inductance and capacitive coupling of the antenna by construction measures and thus reducing the flow of the antenna current, dissipating it, or shifting the resonance frequency. The construction requirements placed on the electrode from a therapeutic aspect only allow little play for this purpose, however.

Furthermore, in contrast to the very simplified consideration used here, antennas also have further resonance frequencies, so that the shift of the resonance behavior of their electrode may possibly again meet the resonance condition in an MR device using other HF frequencies. This path is therefore not advantageous.

Furthermore, EP 0 884 024 B1 is to be cited as technological background, in which a capacitor is connected between the supply lines for the ablation pole of an ablation catheter and a measuring pole, also situated thereon, for recording ECG signals. Because of this capacitor, high-frequency energy may be delivered for ablation via the ablation electrode and ECG signals may also be recorded simultaneously.

US 2006/0009819 A1 discloses a cardiac pacemaker having an elongate electrode which is connected to a pulse generator connector. A passive lossy circuit is provided, which is electrically connected between a distal section of the electrode supply line and a high-frequency grounded surface. The passive lossy circuit has a high-frequency impedance which is approximately equal to a characteristic impedance of the electrode in its implanted state in the body. The reflection of incident waves is thus minimized at the terminals of the lossy circuit and their energy is intentionally dissipated here. The passive lossy circuit also acts as a low-pass filter, because of which the electrode is functional in normal operation of the cardiac pacemaker.

A further example of such an electrode is described in US 2006/0200218 A1. A solution is suggested therein, in which the electrode sheath at least sectionally comprises frequency-dependent insulating material having a lesser conductivity at lower frequencies, while the at least one supply line is produced in a known way and comprises typical material. The frequency dependence of the electrode sheath is implemented by a polymer composite which has dielectric properties. A capacitive coupling of the electrode supply line to the external medium is thus possible. However, this capacitive coupling leaves high effectiveness to be desired. This is because the resistive frequency-independent component of such a capacitive coupling is constant, because of which the total impedance upon HF incidence of an electromagnetic wave may not assume arbitrarily small values.

BRIEF SUMMARY OF THE INVENTION

Starting from the problems described at the beginning, the present invention is based on the object of refining an electrode for interventional purposes in such a way that it may be placed even in radiation fields of MR diagnostic devices without relevant risk to the wearer in a constructively simple way. In particular, simple and cost-effectively producible materials are to be used, which allow a targeted effective and sufficient worsening of the properties of the electrode in regard to its antenna characteristic, without current concentrations and corresponding excess heating being able to occur at electrode poles, in particular around the tip of the electrode.

This object is achieved in that the first and/or second material is manufactured in such a way that it contains conductive particles embedded in a polymer matrix in a concentration which is greater than or equal to the percolation threshold. These may preferably be various materials and/or various concentrations, because the percolation threshold results individually for various materials. Specifically, it has surprisingly been established that the real component, i.e., the ohmic component, of the typically complex conductivity is also subject to change in the event of changing incident frequency. This effect was studied in a material composite made of an electrically conductive plastic having carbon nanotubes (CNT) and is visible above all around the so-called percolation threshold. The ohmic conductivity also surprisingly increases with the frequency for the pure polymer, i.e., not doped with carbon nanotubes (CNT) (pure polycarbonate was studied), but the effect is still too little for the requirements here, however.

According to a first aspect of the present invention, the concentration of conductive particles in the first material is set in such a way that the conduction resistance R increases with rising frequency of an incident electromagnetic wave. According to a further aspect, the concentration of conductive particles in the second material is set in such a way that the sheath resistance r decreases with rising frequency of an incident electromagnetic wave. These aspects have the advantage that, in a simple way and using materials to be produced simply, the property that the effect of radiation fields of magnetic resonance diagnostic devices on the electrode may be almost completely compensated for may thus be exploited effectively.

A further object is seen as providing a production method for an electrode for interventional purposes according to the present invention, which offers secure MR compatibility of the line.

This object is achieved by a method in which a supply line sheath having a lumen is provided and subsequently a supply line is installed in the lumen. In a preferred design, the method comprises the third step of airtight embedding of the supply line in the continuous lumen using a conductive liquid.

As will be clear from the later consideration of the background of the present invention in the scope of the description of exemplary embodiments, according to the present invention, the quality of the oscillating circuit which the electrode forms together with the body as the antenna is reduced enough that on one hand the energy absorbed by the antenna is reduced and on the other hand the losses are distributed in the overall formation of electrode conductor/insulation/body in such a way that excess current concentration does not occur at specific points. This may be achieved by increasing the line resistance R of the supply line, by reducing its sheath resistance r, or by both.

The essential advantage of reducing the quality of the antenna in relation to a band filter is that the mode of operation is independent of the resonance frequency of the antenna and of the frequency of the incident electromagnetic alternating field, i.e., the energy absorbed by the antenna, is reduced by the quality factor at all frequencies. In this way, the achievement of the object according to the present invention works equally in various MR devices having various operating frequencies.

BRIEF DESCRIPTION OF THE DRAWINGS

Preferred embodiments of the electrode in different variants are specified in the dependent claims. Their features, details, and advantages result from the following description, in which exemplary embodiments of the subject matter of the present invention are explained in greater detail on the basis of the attached drawings.

FIG. 8 shows a schematic view of the distal end area of an electrode, FIG. 9a/9b show a schematic illustration of the detail of medial sections of various electrodes according to the present invention having cable supply lines, FIG. 10a/10b show a schematic illustration of the detail of medial sections of alternative various electrodes according to the present invention having at least one coiled section, FIG. 11a/11b show a schematic illustration of the detail of medial sections of bipolar electrode lines, and FIG. 12a/12b show a schematic illustration of optional embodiments of distal tip or ring electrode poles of various electrode lines according to the present invention.

DETAILED DESCRIPTION OF THE INVENTION

Firstly, the following fundamental statements on the oscillation behavior of antenna circuits are to be given on the background of the present invention:

If a preferably elongate electrical conductor is located in the room, this conductor acts as an antenna for electromagnetic radiation which floods through the room. The antenna converts the free space wave into a line wave, through which antenna currents flow. This situation exists, for example, if a patient having implanted cardiac pacemaker electrodes is subjected to an electromagnetic alternating field. The currents which arise in the electrode supply line acting as an antenna are conducted into the body at the contact points to the tissue and essentially converted into heat there. Depending on the strength of the electromagnetic alternating field, the extent of the heating may be hazardous to the patient. Alternating fields of hazardous strengths to pacemaker wearers occur—as noted—in MR tomographs, for example.

Figure 1:
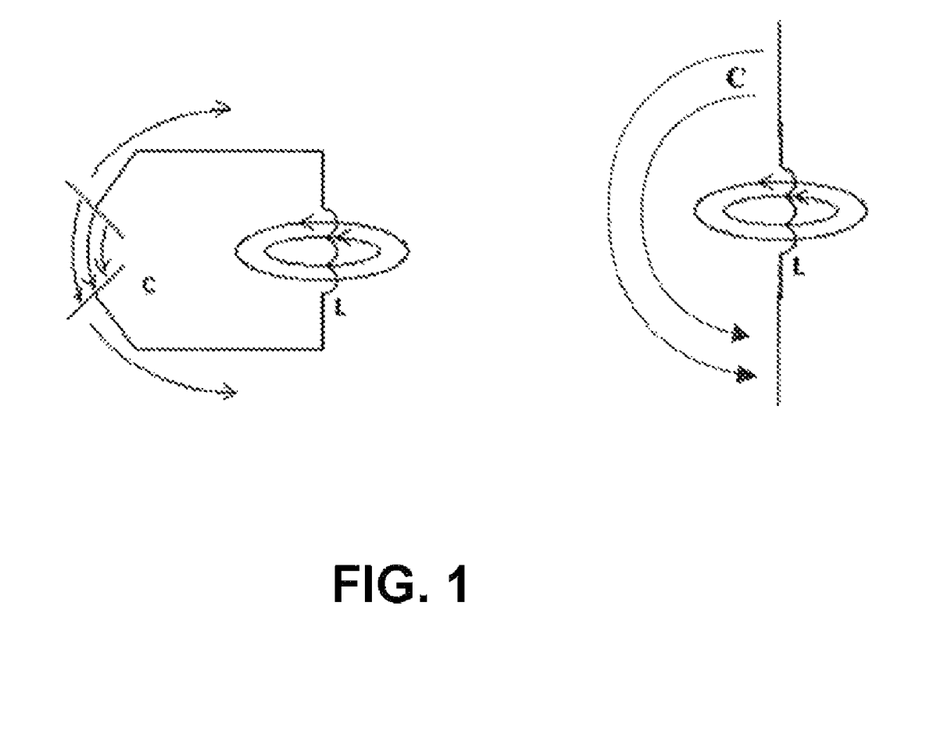
FIG. 1 shows a schematic diagram to illustrate the simplified functional principle of an antenna as an open oscillating circuit.

In a simplified description, an antenna represents an open oscillating circuit, which may be understood as if the capacitor plates of a closed oscillating circuit have been pulled apart into an elongate shape (FIG. 1). This simplified illustration describes the behavior of an antenna only in broad strokes, but it is sufficient to explain the principle on which the present invention is based. In this illustration, the antenna rod A embodies an inductance L, whose ends are capacitively coupled to one another (capacitance C). The antenna current reaches its maximum amplitude when resonance exists, i.e., when the oscillating circuit is driven at the resonance frequency $f_0$. The resonance frequency of the oscillating circuit shown in FIG. 1 is $$f_0 = \frac{1}{2\pi\sqrt{LC}}.$$

Figure 2:
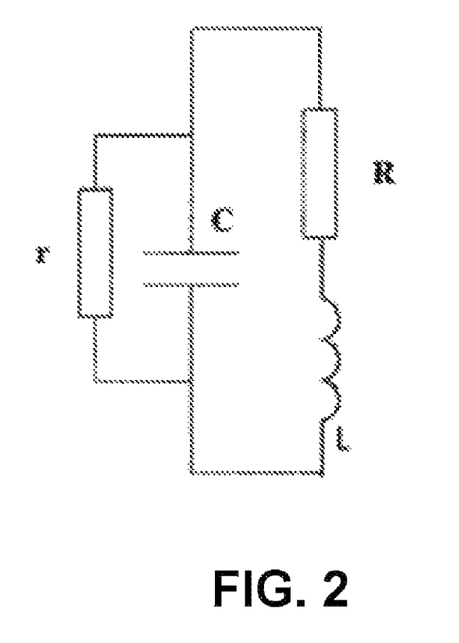
FIG. 2 shows a replacement circuit diagram of the electrode supply line as an oscillating circuit having ohmic losses.
Figure 3:
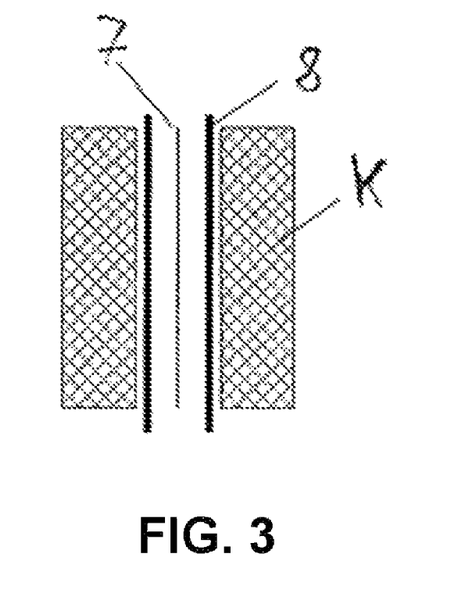
FIG. 3 shows a schematic illustration of an electrode body having supply line and electrode sheath in its body environment.

In reality, the components L and C are lossy, i.e., the inductance has an ohmic resistance R connected in series, while an ohmic resistance r is connected in parallel to the capacitance (see FIG. 2). In the case of the pacemaker electrode 2, as shown in FIG. 3, the electrode supply line 7 represents the antenna rod. It has an inductance L and a line resistance R as a function of the geometry and the material properties. The capacitive coupling of the distal line sections occurs via the surrounding dielectric medium (this includes the electrode insulation 8 and body K). Ohmic losses of the insulation and the body are summarized in the replacement circuit diagram in FIG. 2 by the resistance r. For the function as a pacemaker electrode, the electrode supply line 7 is to conduct as well as possible in the longitudinal direction (i.e., R is as small as possible), but the insulation 8 is very good (i.e., r is as large as possible), in contrast, for both the stimulation and also for the perception of the stimulus response (sensing). These ohmic components act on the quality Q of the oscillating circuit, which is a measure of how high the antenna currents may be at a given intensity of the electromagnetic radiation. The quality is calculated as a quotient $$Q = \frac{f_0}{B},$$

in which $f_0$ is the resonance frequency and B is the bandwidth. The bandwidth is defined by the limiting frequencies (f=f1, f=f2), outside of which the absolute value of the conductivity |Y| sinks below $1/\sqrt{2}$ of the maximum value.

In the case of the oscillating circuit from FIG. 2:

$$|Y| = \left| \frac{1}{R + j2\pi fL + \frac{1}{1/r + j2\pi fC}} \right|, (j = \sqrt{-1}).$$

The quality of the oscillating circuit (and thus also the maximum possible antenna current) is especially good for known electrodes, i.e., it rises with decreasing R and increasing r. This has an effect especially in the case of resonance. As a result of the physiologically required electrode length (of approximately 40-60 cm), the dielectric properties of the body, and also the typical construction, the resonance condition occurs very close to the Larmor frequency for hydrogen of approximately 64 MHz in 1.5 T MR devices. At a typical inductance of 3 µH of the electrode supply line and a capacitance of approximately 2 pF, for example, the resonance frequency of the observed oscillating circuit is $f_0$=64.97 MHz.

Figure 4:
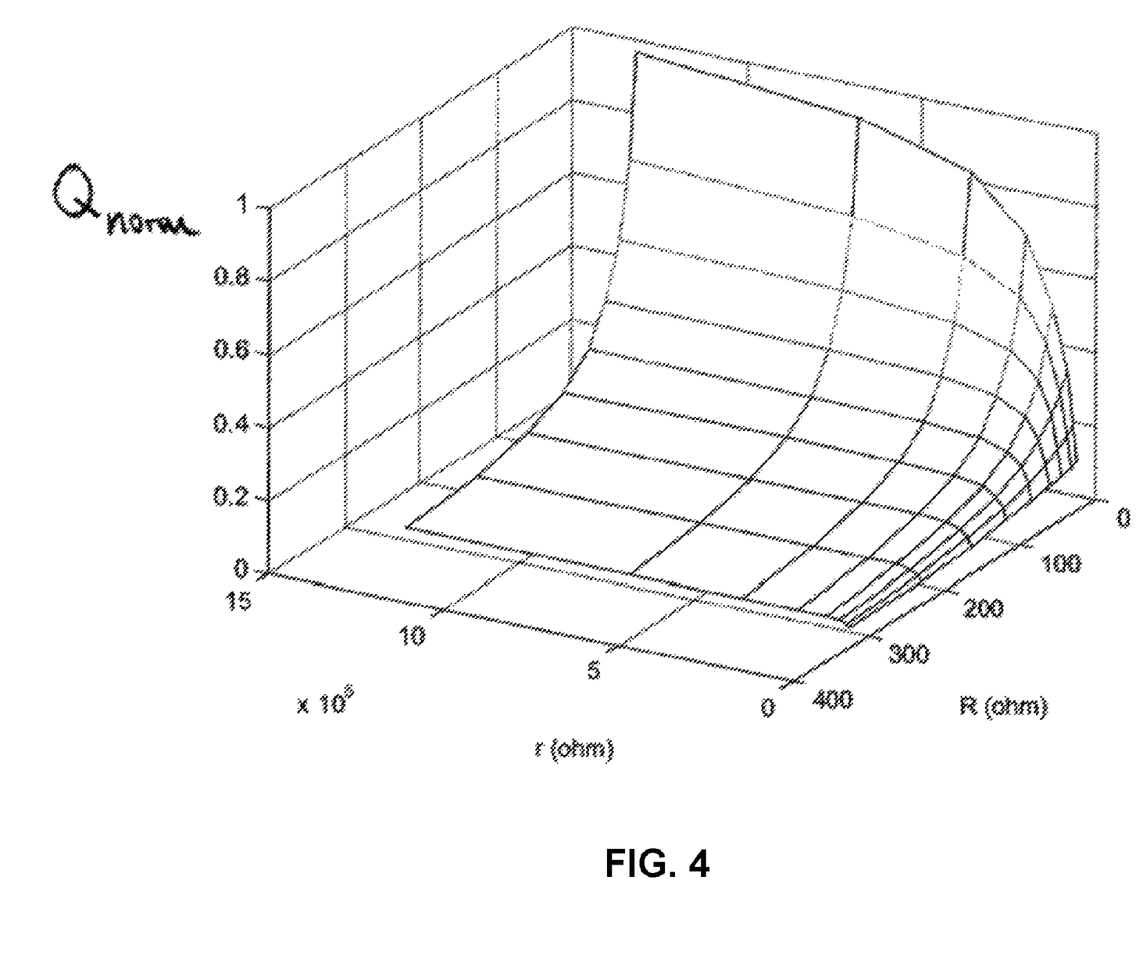
FIG. 4 shows a diagram to illustrate the dependence of the normalized oscillating circuit quality on the ohmic resistance components of the capacitance and inductance of the replacement circuit diagram oscillating circuit from FIG. 3, FIGS. 5a/5b show a schematic illustration of the construction of an electrode according to the present invention and a replacement circuit diagram to describe the electric material properties FIG. 6a/6b show a diagram to illustrate the dependence of the ohmic component of the inductance (a) on the frequency and (b) on the concentration of the conductive particles (carbon nanotubes here)

For illustration, FIG. 4 shows the dependence of the quality of the lossy oscillating circuit from FIG. 2 on the ohmic loss resistances R and r within value ranges relevant in practice, L=3 µH and C=2 pF being assumed. The shape of this dependence is also qualitatively similar for L and C deviating significantly therefrom.

As shown in FIG. 4, the quality of the antenna may expediently be worsened in that the resistance r of the antenna sheath is reduced, the resistance R of the antenna line is increased, or both measures are taken.

Therefore, the achievement of the object according to the present invention comprises changing the properties of the electrode to influence the antenna properties in such a way that current concentrations and thus accompanying excess heating at the electrode poles may not occur in radiation fields. The electrode comprises means which reduce the quality of the oscillating circuit which the electrode forms together with the body as the antenna enough that on one hand the energy absorbed by the antenna is reduced and on the other hand the losses are distributed in the overall formation of electrode line/insulation/body in such a way that excess current concentrations do not occur in specific points.

According to the prior art, the typical electrode insulation may be replaced on one hand by a less-insulating material, to thus reduce the sheath resistance of the electrode supply line to the body, worsen the quality of the antenna, and minimize the antenna currents induced in the electrode supply line and thus the heating caused in the presence of electromagnetic alternating fields. At an existing line resistance of the typical cardiac pacemaker electrode supply line of approximately 50 ohm and a reduction of the sheath resistance (in the meaning of the replacement circuit diagram from FIG. 2) from >1 Mohm to 10 kohm, for example, the quality of the oscillating circuit is reduced by approximately a factor of 10. Arbitrary reduction of the sheath resistance is not possible in this embodiment, however, because the stimulation pulse may also be dissipated via the no longer ideal supply line insulation and thus damped or may unintentionally stimulate surrounding tissue. The practical limit is a function of the line resistance, the tissue resistance, the tissue sensitivity, and the size of the stimulation pulse. Especially in cardiac pacemaker electrodes, this limit may be approximately 1 kohm.

On the other hand, the line resistance of the electrode supply line may be increased according to the prior art. It is to be ensured that the line resistance is not increased too strongly, because this worsens the properties as an electrode and endangers the function of the electrode. The therapeutic effectiveness would thus be impaired by the increased losses within the electrode. Typical cardiac pacemaker electrodes have line resistances up to approximately 100 ohm. An increase to approximately 200 ohm is still therapeutically tolerable, however. ICD electrodes may not exceed a line resistance of a few ohm (in the single-digit ohm range), therefore, this solution approach is not or is hardly applicable for them.

To increase the effectiveness, the two solution approaches just described may be optimally combined, i.e., both reducing the sheath resistance of the electrode sheath and also increasing the line resistance of the electrode supply line, so that the quality is reduced as well as possible as shown in FIG. 4. This approach is especially suitable for cardiac pacemaker and neurostimulation electrodes, as is already known from US 2006/0200218 A1.

However, the disadvantage of this solution from US 2006/0200218A1 is that the optimization and increase of the effectiveness is only possible in a limited way, because the sheath resistance and the line resistance are fixed. I.e.: if the sheath resistance is set low and the line resistance is set high to prevent the heating of the line under HF radiation of an MR device, the electrode no longer stimulates correctly. The high line resistance R prevents sufficient stimulation energy from reaching the tissue. Stimulation energy is dissipated and does not reach the tissue to be stimulated due to the low sheath resistance. However, if the sheath resistance is increased and the line resistance is lowered so as not to endanger the treatment, the electrode heats up too strongly in an HF field of an MR device. The subject matter cited in US 2006/0200218A1 thus does not achieve the object.

To achieve the object of reducing the antenna quality, it is necessary according to the present invention to reduce the resistance r of the electrode sheath and/or increase the line resistance R. Because the therapeutic use only occurs at low frequencies (less than 1 MHz) and the antenna quality must only be reduced for high frequencies (greater than or equal to 1 MHz) (HF radiation of an MR device currently in the range 21 MHz for 0.5 Tesla MRT and 300 MHz for 7 Tesla MRT), according to the present invention, both the sheath resistance r and/or the line resistance R of the electrode are frequency-dependent, in such a way that the sheath resistance r decreases with increasing frequency and/or the line resistance R increases with increasing frequency. This is true in particular for frequencies greater than 1 MHz.

Figure 5A:
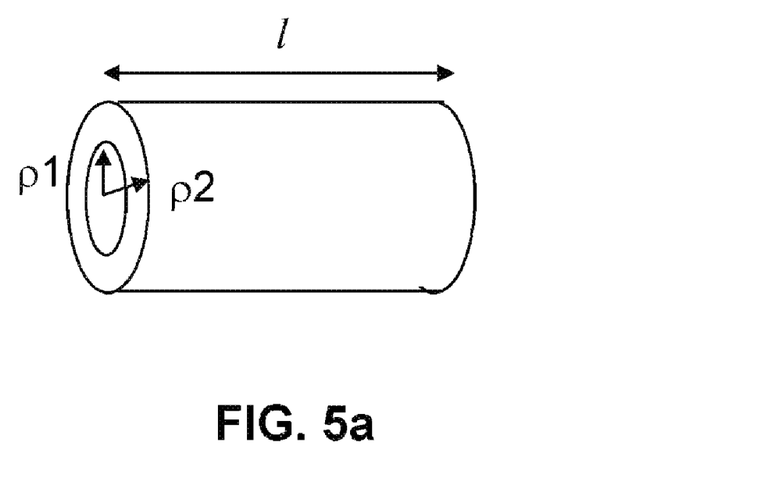
Figure 5B:
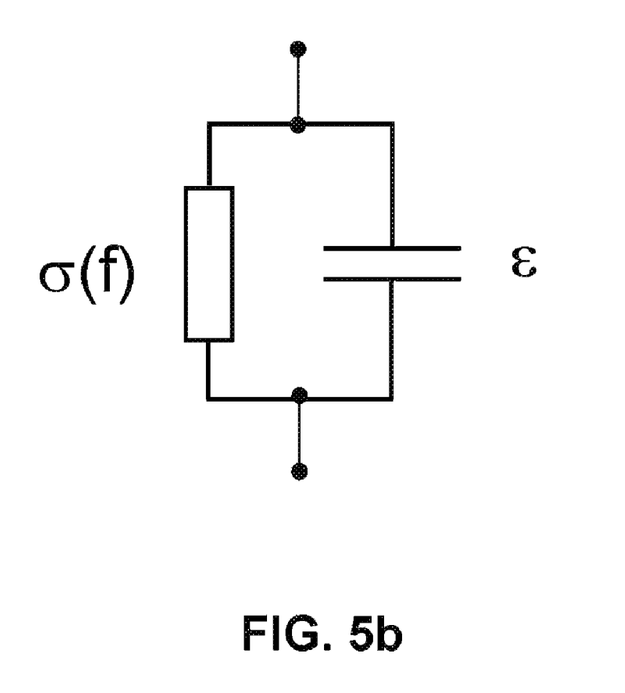

In other words, the absolute value of the admittance in the radial direction (perpendicularly to the electrode longitudinal direction) is very generally calculated for an electrode sheath having a geometry from FIG. 5a and an electrical replacement circuit diagram from FIG. 5b as follows:

$$|Y_a(f)| = \frac{2\pi l}{\ln\frac{\rho_2}{\rho_1}} \sqrt{\sigma_a^2 + (2\pi f)^2 \varepsilon^2}.$$

In case of the polymer composite used according to the present invention, the ohmic resistance is itself frequency-dependent, i.e., $\sigma_b = \sigma_b(f)$. Therefore:

$$|Y_b(f)| = \frac{2\pi l}{\ln\frac{\rho_2}{\rho_1}} \sqrt{\sigma_b^2(f) + (2\pi f)^2 \varepsilon^2}.$$

According to the present invention, the first material of the electrode supply line and/or the second material of the electrode sheath are to be selected and/or combined in such a way that the resistance values r and R change as a function of frequency. In this embodiment, a reduction of the sheath resistance r and/or an increase of the line resistance R preferably occur at high frequencies (i.e., at frequencies typical for MR devices).

Furthermore, in this embodiment, the parameters of the second material—in particular the concentration of conductive particles in the second material—and, for example, additionally the thickness of the sheath are preferably selected in such a way that the sheath resistance r decreases with increasing frequency. In particular, the cited properties of the second material (or, in other words, of the second material composite) are selected in such a way that for frequencies below 1000 Hz a sheath resistance r greater than 1 Mohm results, for frequencies above 5 MHz a sheath resistance r less than 10 kohm results, and for frequencies above 20 MHz, a sheath resistance r less than 1 kohm results.

In contrast, the line resistance R of the electrode line is set by selection of suitable parameters of the first material—in particular the concentration of conductive particles in this first material—in such a way that a higher line resistance R results with increasing frequency. In particular, the line resistance R of the first material (or of the first material composite and other words), results in such a way that it has an overall value of less than 100 ohm for frequencies below 1000 Hz and a value greater than 500 ohm for frequencies above 20 MHz. In a preferred embodiment, the line resistance R even increases, at a maximum frequency of 300 MHz in a 7 Tesla MRT, to more than 20 times the value of 100 ohm, i.e., greater than 2 kohm, preferably greater than 4 kohm Such frequency-dependent conductive materials—which both the first and also the second material represent—may be produced by emitting conductive materials (also referred to as conductive particles), in particular nanoparticles, in an electrically insulating matrix. These particles are to have an elongate shape, the conductive particles preferably have a length to width and/or diameter ratio of greater than 2, especially preferably greater than 100. In a special embodiment, carbon particles having dimensions in the single-digit to double-digit nanometer range are introduced into a polymer matrix (described, for example, in L. J. Adriaanse, et al.: High-Dilution Carbon-Black/Polymer Composites: Hierachical Percolating Network Derived from Hz to THz ac Conductivity., Physical Review Letters, vol. 78, No. 9, March 1997). The frequency characteristic of the material is set via the concentration of the conducting nanoparticles. Further examples of such preferred conductive particles are carbon fibers having a preferred length/diameter ratio greater than 10, conductive soot, carbon black, and/or metal particles. These carbon particles are coated using a metal or an alloy in a further preferred embodiment. For example, aluminum (Al) or nickel (Ni) are suitable as metals for the particles and also for the coating, however, biocompatible metals, such as platinum (Pt), iridium (Ir), or gold (Au) are also preferred. Preferably those alloys made of the cited metals come into consideration as the alloy. Another preferred embodiment uses frequency-dependent conductive polymer composites instead of carbon/metal particles as the conductive additive.

Carbon nanotubes (CNT) are still more effective than carbon/metal nanoparticles. A significantly smaller quantity of such nanotubes is required in comparison to nanoparticles to implement a specific conductivity characteristic.

As noted, the frequency dependence of the real component in particular—in other words, the ohmic component—of the typically complex conductivity is the subject matter of the present invention.

Figure 6A:
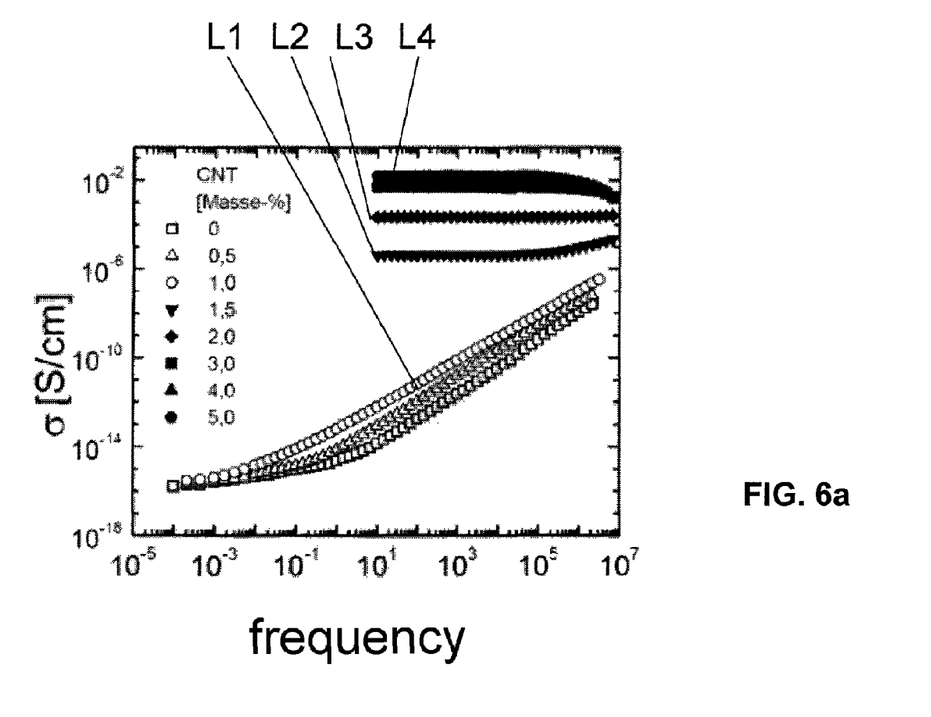
Figure 6B:
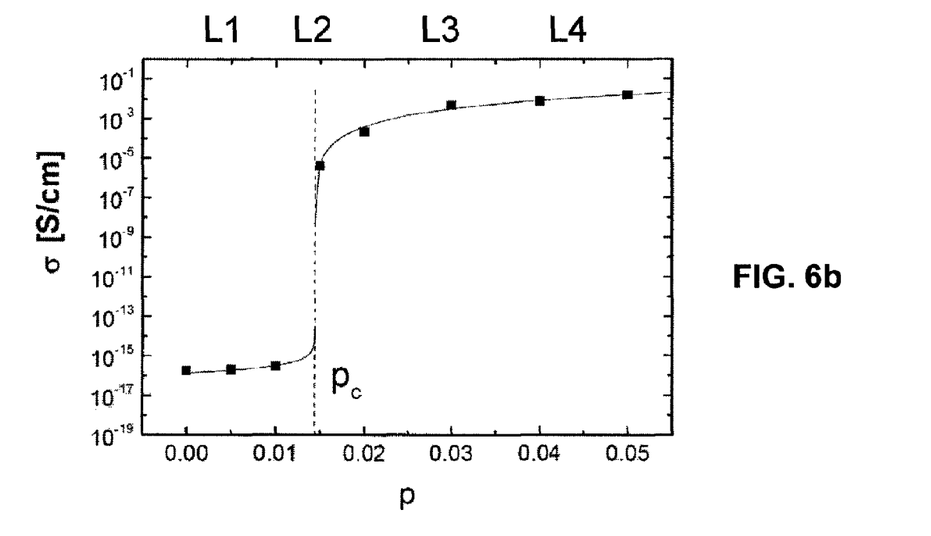

FIGS. 6a and 6b show the dependence of the real, i.e., the purely ohmic component of the conductivity o of a polymer composite which is enriched using carbon nanotubes (CNT). It is surprising that the ohmic conductivity also increases with the frequency for the pure polymer, i.e., not doped with carbon nanotubes (CNT) (pure polycarbonate was studied). However, the effect is still too small overall for the requirements placed here.

FIG. 6a shows the dependence of the conductivity σ on the frequency at various concentrations of the conductive particles CNT in the polymer composite.

FIG. 6b shows the dependence of the conductivity σ on the concentration p of the conductive particles CNT at a selected frequency.

For the frequency dependence of the real, i.e., the purely ohmic component of the conductivity, one differentiates between four conductive modes L1 through L4, which are determined by the concentration of the conductive particles in the polymer and are marked in FIGS. 6a and 6b:

L1: Below a specific concentration threshold, referred to as the percolation threshold (identified in FIG. 6b by "pc"), the conductivity is generally at a low level and is hardly dependent on the conductive particle concentration. It does increase with frequency, but this is not usable for the purpose of the present invention because of the low level.

L2: In proximity to the percolation threshold, the conductivity is significantly higher than L1, in particular in the low-frequency range, so that the conductivity is at a significantly higher level than in the conductive mode L1. In addition, it increases with rising frequency.

L3: At still higher concentrations, the conductivity is frequency-independent.

L4: If the conductive particle concentration is increased further, the frequency dependence reverses, i.e., the very high conductivity at low frequencies decreases toward higher frequencies.

In a preferred embodiment of the achievement of the object according to the present invention, the second material of the type described above is used in the conductive mode L2 to implement an electrode sheath whose sheath resistance r thus decreases with rising frequency.

Alternatively or additionally, a first material of the type described above is used in the conductive mode L4 for the frequency-dependent implementation of at least a part of the electrode supply line, the line resistance R of the electrode supply line also rising with rising frequency due to this at least one part. The electrical behavior of these materials may thus be modeled by a replacement circuit diagram as specified in FIG. 5b. The resistive component is identified hereby the conductivity $\sigma$, which is frequency-dependent ($\sigma=\sigma(f)$) according to the present invention and in contrast to US 2006/0200218 A1 and which changes with the frequency depending on the conductive mode set. The material suggested in US 2006/0200218 A1 is unsuitable for implementing a frequency dependence (conductive mode L4) of the line resistance R.

The present invention provides predominantly using silicone, polyurethane, and/or polyether block amide, also known as PEBAX™ or a silicone-polyurethane copolymer as the polymer. Types which are used in typical electrode sheaths, and doping them using the preferred conductive particles described above, are preferred.

A conductive polymer composite of the type according to the present invention is not producible using any type of conductive particle, at least not at concentrations which lie below the saturation and/or processability threshold. In highly saturated polymer composites, the mechanical properties change unfavorably, for example, the material becomes brittle and is finally unsuitable for use in intracorporeal electrodes A selection of conductive materials with the associated concentrations for reaching the conductive modes 2 or 4 is listed in the following table:

| Conductive particle | Conductive mode L2 | Conductive mode L4 |
| --- | --- | --- |
| CNT | 1.25-1.75% | >3% |
| Carbon fibers | 5-10% | >20% |
| Carbon Black: CB | 8-20% | >30% |
| Metal-coated carbon | 10-20% | >25% |

As described, the first material is preferably in conductive mode L4, which preferably means that the proportion of conductive particles in the first material is greater than 2 mass-%, preferably between 3 and 20 mass-%, and especially preferably between 3 and 10 mass-%.

On the other hand, as noted, the second material is preferably in conductive mode 2, which means that the proportion of conductive particles in the second material moves in the range between 1.25 and 20 mass-%, preferably between 1.25 and 10 mass-%, especially preferably between 1.25 and 1.75 mass-% of the total volume.

For this material, in conductive mode L2, for frequencies 1 MHz, the following equation always applies $\sigma_b(f_2)>\sigma_b(f_1)$, if $f_2>f_1$. Therefore, the following equation always applies according to the above-mentioned formula:

$$|Y_b(f)|>|Y_a(f)|$$

According to the present invention, the external mantle of the electrode body, which is a good insulator in typical electrodes (e.g., silicone or polyurethane) is implemented from the second material described, the electrode supply line having direct electrical contact to this material. In coaxially constructed multipolar electrodes, in one embodiment, only the external conductor having an external sheath comprises the second material, while the internal conductor is typically insulated using a frequency-independent internal sheath. In further embodiments, the frequency-independent insulating material of the internal sheath of selected or all internal conductors is also replaced by the second material. At high frequencies, the entire electrode body thus behaves like a thick conductor, which is hardly insulated from the tissue, i.e., the sheath resistance r is small, therefore less heating is caused upon HF radiation, because the resulting antenna has a very poor quality.

In a further embodiment, the contact surface of the second material is metal plated (e.g., by a coating or vapor-deposition method) and/or enclosed by a metal mantle (e.g., ring or coil) toward the surrounding medium (body tissue or blood).

Figure 7:
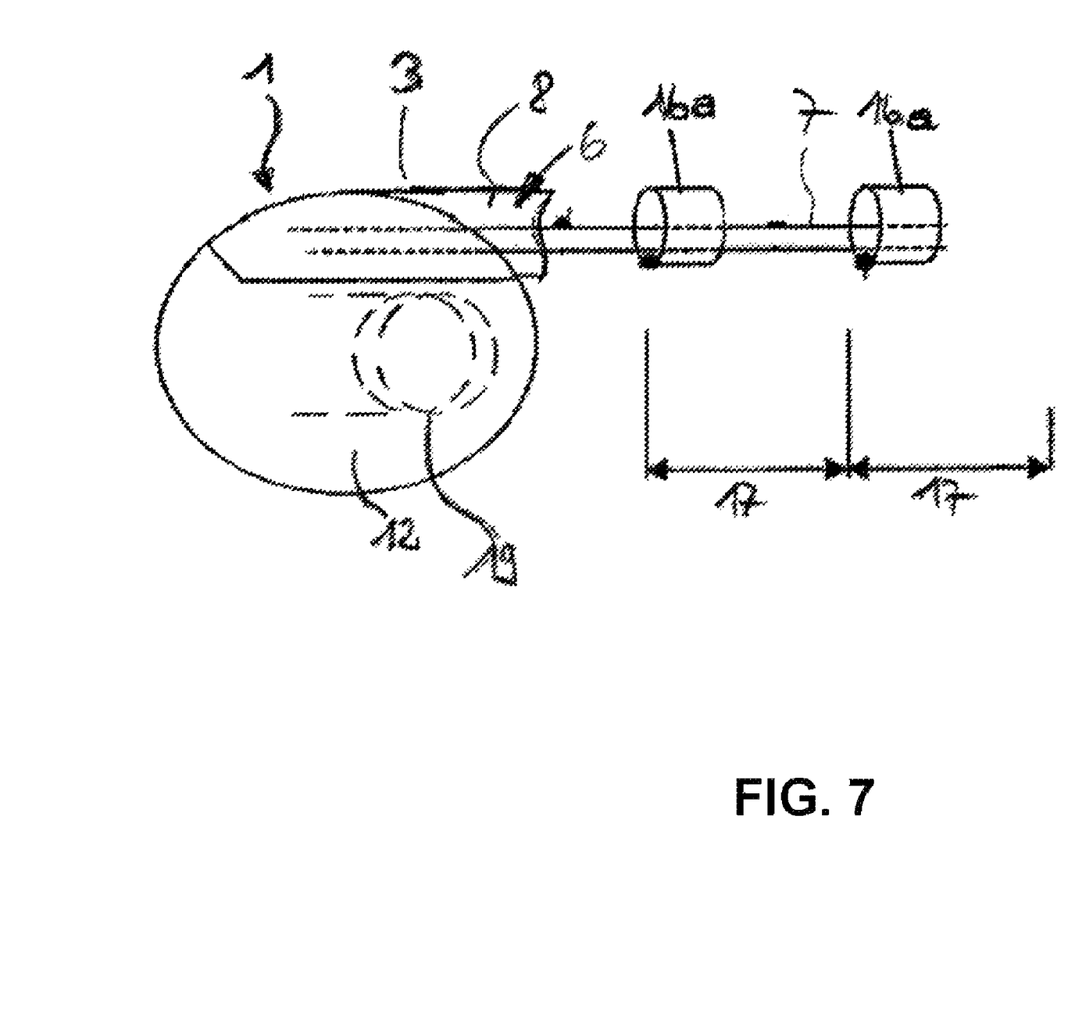
FIG. 7 shows a schematic illustration of a cardiac pacemaker having a pacemaker electrode.

A cardiac pacemaker 1 having housing 12 is shown schematically in FIG. 7, on which the proximal end 3 of an electrode 2 placed in the heart is connected in a typical way. The distal end 4 of the electrode 2 is provided with a tip electrode pole 5, via which stimulation pulses may be delivered to the heart, for example. For this purpose, an insulated supply line 7 runs to the tip electrode pole 5 in the elongate electrode body 6.

Only sections 16a of the sheath 8 and/or the supply line 7 are implemented from the first and/or second material in this case. These sections are shown as electrode body segments 16a in FIG. 7. They are implemented here as cylindrical segments, which are completely filled by the second material. In the case of a multipolar electrode, this second material contacts all or only selected electrode supply lines.

In a further embodiment, these electrode body segments just described are distributed multiple times at specific intervals over the electrode supply line length, the contact pattern, i.e., the sections at which the conductor(s) 7 are electrically in contact with the sheath made of a second material, being able to be identical or different in all of these electrode body segments. In one variant of this embodiment, the intervals 17 of these electrode body segments are all less than ¼, preferably ⅒ of the wavelength of the HF ways in the operating medium. The operating medium is preferably a physiological body such as a human or animal body. For example, this may be surrounding bodily medium such as body tissue and/or blood.

In a further embodiment (not shown) different sized intervals 17 and, furthermore, optionally different contact patterns are implemented in that the electrode supply line sections divided by electrode body segments 16a comprising a first and/or a second material are tuned to one another in regard to their wave impedances in such a way that predominantly unidirectional reflections occur at their transitions in the direction of the proximal electrode side. In this way, the undesired power transmission in the direction of the electrode pole connected to the tissue is to be reduced. This principle is described in Bonmassar, G.: "Resistive Tapered Stripline (RTS) in Electroencephalogram Recordings during MRI". IEEE Transactions on Microwave Theory and Techniques, vol. 52. No. 8, August 2004.

In a further alternative embodiment (not shown) the second material located between the electrode body segments 16a spaced apart in the longitudinal direction may additionally also be sectionally implemented in the radial direction. A construction of layers made of frequency-independent insulating material and second material lying coaxially around the longitudinal axis of the electrode is provided. The combination of these two different materials may especially preferably repeat arbitrarily in the radial direction.

In a special embodiment, the non-homogeneously distributed electrical properties required for this purpose, i.e., the locally differing conductivity and/or frequency behavior of the material, are implemented by selective doping of the polymer matrix by conductive particles.

Finally, a transponder antenna 19 is indicated in the cardiac pacemaker 1 in FIG. 7, with the aid of which the cardiac pacemaker 1 may be parameterized externally and/or data may be transmitted outward therefrom. The transponder antenna 19 may simultaneously be used for detecting a high-frequency radiation, as is radiated in the course of a magnetic resonance diagnosis in an MR tomograph, for example. This information may be used, in case of an actively controllable design of the coupling elements, to drive them accordingly. The function of the transponder antenna 19 may also be assumed by the supply line 7 itself or the housing 12 of the cardiac pacemaker 1.

In order that the intended effect is applied especially well by the electrode sheath made of a second material, it must be ensured that the supply line 7 is in continuous contact with this material. This is because air inclusions between the supply line 7 and the sheath act as individual insulators and cancel out the desired effect.

Therefore, in a preferred design of the electrode line according to the present invention, the supply line 7 is embedded in the lumen in the supply line insulation 8 using a conductive and curable liquid. It is thus ensured that no air inclusions occur. The conductive liquid—preferably also gelatinous—is preferably a conductive polymer curable under the effect of energy.

The production method connected thereto comprises the following work steps:
  providing a supply line sheath (8) having a continuous lumen from the proximal end up to an electrode pole located at the distal end,
  installing a supply line in the continuous lumen.

In addition, the airtight embedding of the supply line in the continuous lumen using a conductive liquid may be a third subsequent step.

Figure 8:
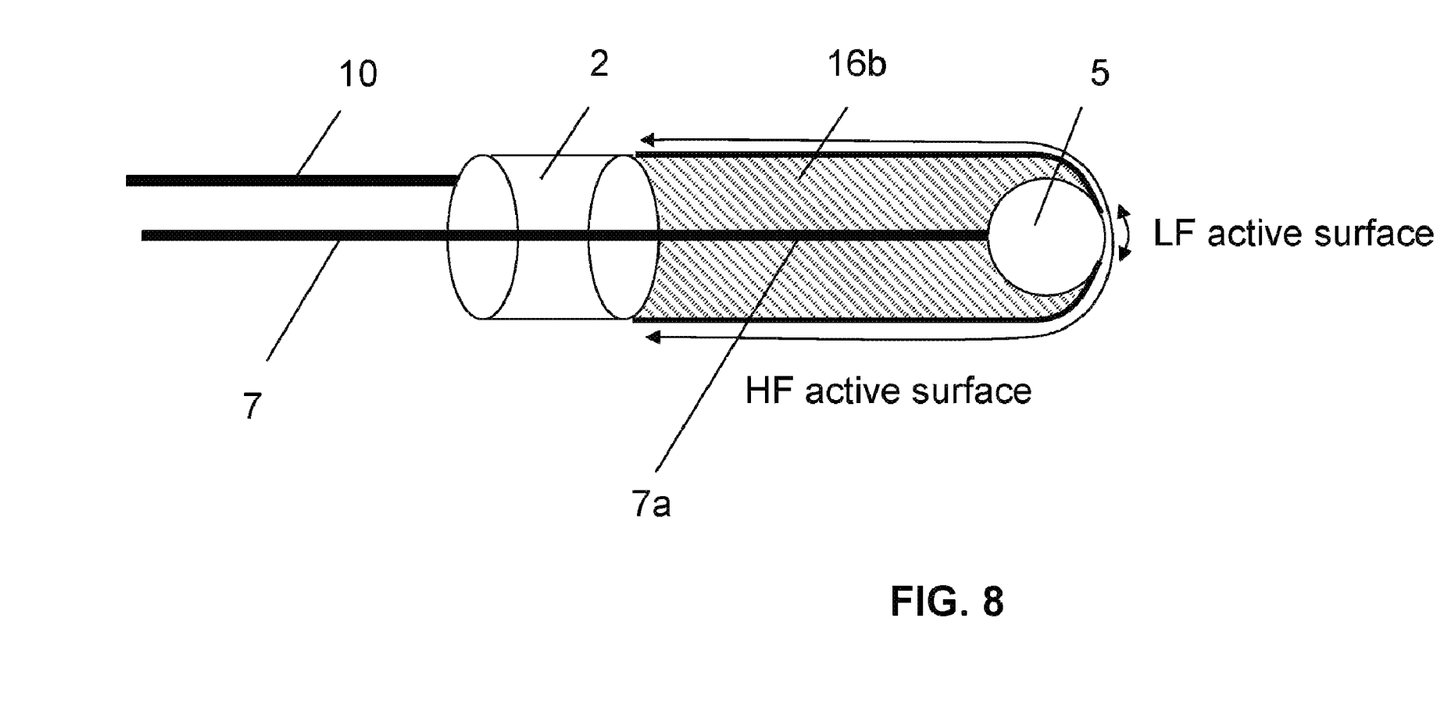

In a further exemplary embodiment shown in FIG. 8, at least one electrode pole, e.g., the tip electrode pole 5, is at least partially covered by the second material 16b, as sketched in FIG. 8. The preferably large (in particular large-area) electrode head is covered in such a way that only a small area is conductive for low-frequency (LF) current ("LF active area" in FIG. 8). Stimulation currents may thus be delivered at high current density. For high frequencies (HF), in contrast, nearly the entire electrode head surface has good electrical conductivity ("HF active area" in FIG. 8), so that the current density and thus the developed specific heat remain low.

In a special embodiment, the electrode head sheath 16b made of the second material extends up to the second pole, such as the ring 2 having supply line 10, a bipolar electrode. The section 7a of the inner supply line 7, which contacts the tip electrode pole 5, is not electrically insulated to the second material of the sheath 16b. The second material of the sheath 16b may also extend between two poles of a multipolar electrode. An element 16a as in FIG. 7 may also directly adjoin the ring 2.

As described above, a line resistance R, which grows with rising frequency, of the electrode supply line also causes worsening of the antenna quality. In an embodiment according to the present invention, the electrode supply line is implemented from a material in the conductive method L4 over the entire length. In a further embodiment, a typical electrode supply line is divided into one or more sections which are connected using the cited material. In a preferred embodiment, the length of the sections is less than ¼, preferably ⅒ of the wavelength of the radiated high-frequency fields in the body medium.

Figure 9A:
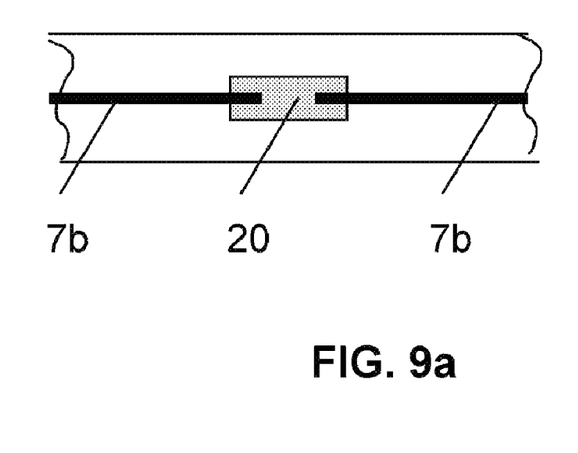
Figure 9B:
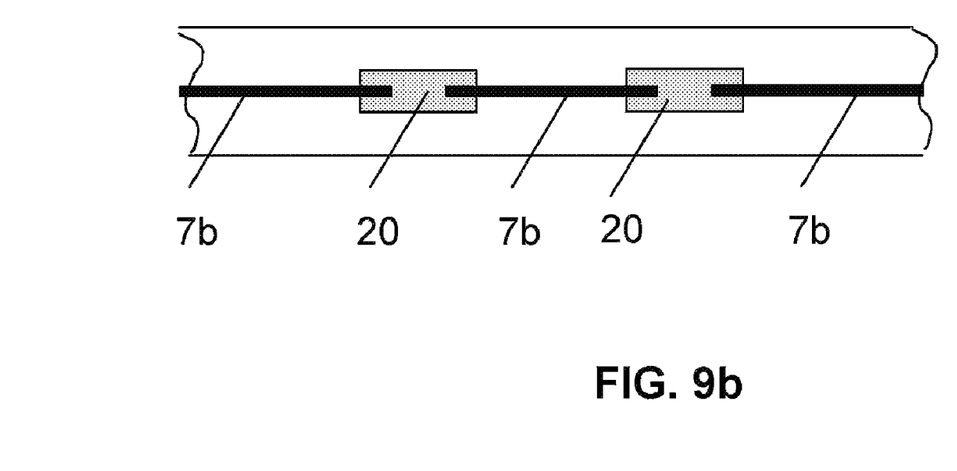

FIGS. 9a and 9b schematically show such transition points. The sections 20 made of the cited material in the conductive mode L4 are shaped cylindrically. Cable-like sections of the electrode supply line 7b penetrate into the cylinder section 20 and end in its depth. The continuation of the line sections 7b preferably begins offset in the longitudinal direction, so that the ends of the line sections 7b located in the cylinder section 20 do not touch. A radial offset of the line sections 7b to one another is also possible, of course, in that either one or both sections 7b which penetrate into the cylinder section 20 are offset radially from the longitudinal axis of the electrode line. The electrode line is produced by the cylinder 20 made of the material in the conductive mode L4. In a further embodiment, the cylindrical sections 20 are implemented as tubes or hoses, through which two sequential line sections may be connected to one another. This embodiment is especially favorable for a simple production process. The value of the resistance is calculated from the geometry of these configurations in the conductivity at a specific frequency.

Figure 10A:
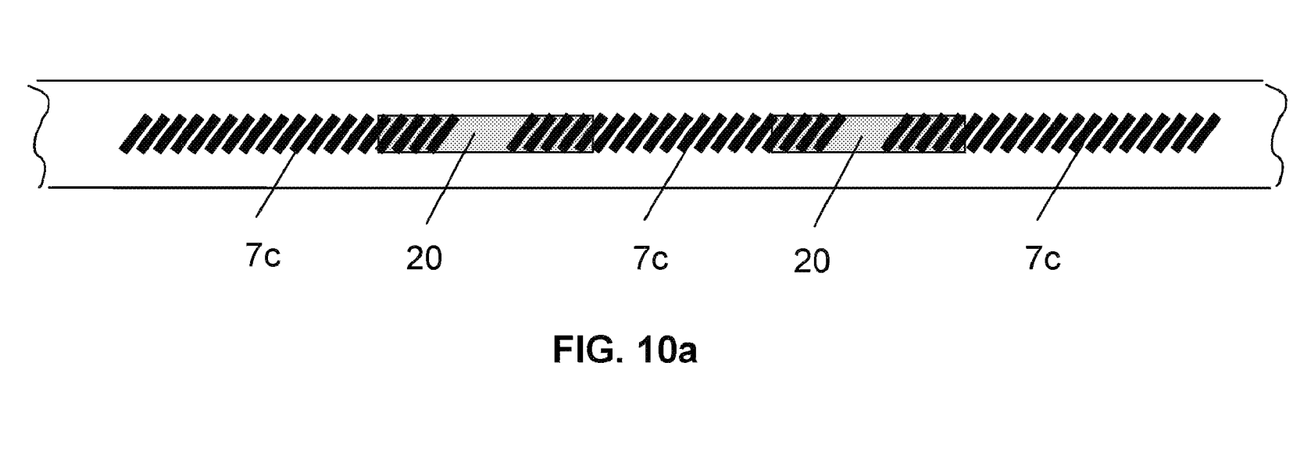
Figure 10B:
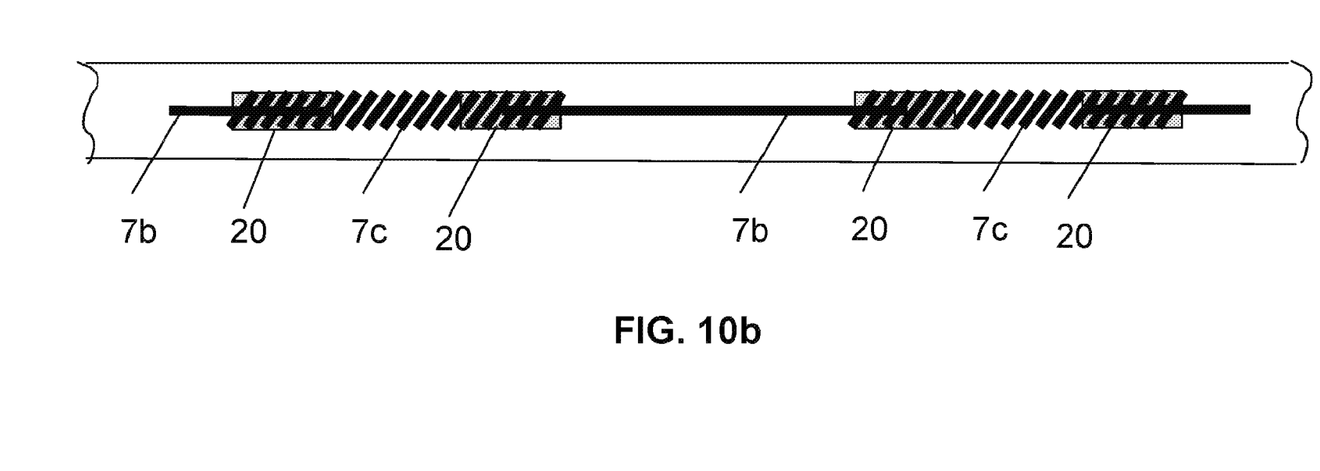

In the case of a coiled supply line, it also winds externally over an area of the mantle surface of the cylinder made of the material according to the present invention. Schematic examples of such solutions are shown in FIGS. 10a and 10b. FIG. 10a shows coiled supply line sections 7c, which wind externally over a partial area of a cylindrical section 20 made of a material in the conductive mode L4. The ends of these coiled sections 7c may be shaped in such a way that they penetrate radially inward and thus end in the depth of the cylindrical section 20. Simply "pushing on" the coiled sections 7c without mutual contact is also sufficient, however. Two coiled sections 7c are—similarly to the embodiment having cable sections 7b from FIGS. 9a and 9b—attached to the cylinder section 20 in such a way that the ends of the coiled sections 7c do not touch. In a further embodiment from FIG. 10b, a combination of coiled sections 7c (as described in FIG. 10a) and cable-like sections 7b (as described in FIGS. 9a and 9b) is possible. Therefore, it must also be ensured in this embodiment that the ends of the coiled sections 7c and the cable sections 7b in the cylindrical section 20 made of the material in the conductive mode L4 do not touch. This may be made possible, for example, in that the coiled sections 7c are pushed onto the cylinder section 20 and the cable section 7b ends in the depth in the cylinder section 20 or may be led up to the end of the cylinder section 20 opposite to the penetration point. A coiled section 7c and a cable section 7b may be attached to each cylindrical section 20, optionally, only coiled sections 7c or cable sections 7b may be fastened to one or more of the cylindrical sections 20.

Figure 11A:
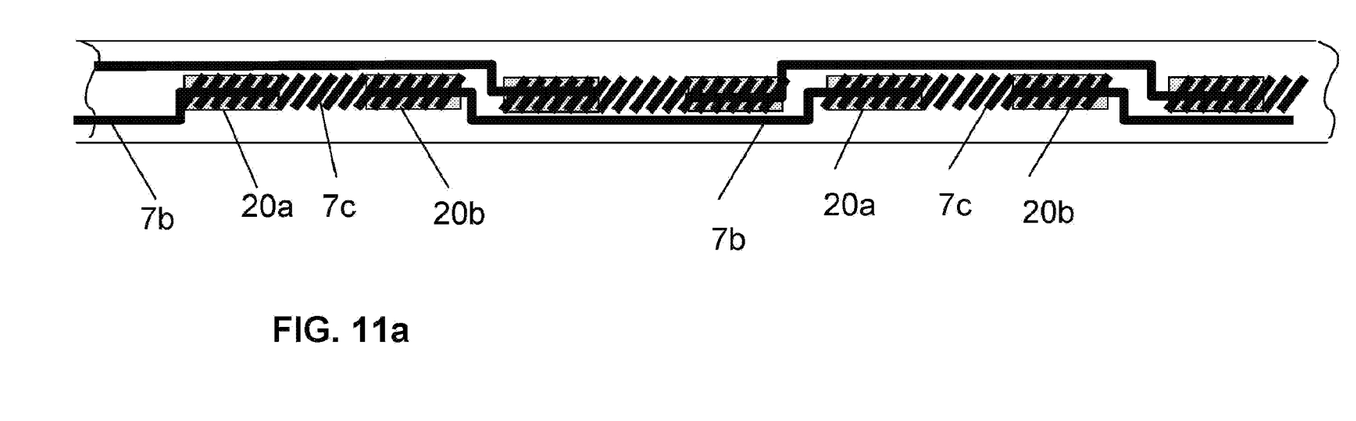

The embodiment just cited may also be implemented in multipolar electrode lines. FIG. 11a shows two supply lines of a bipolar electrode, which lead to two different electrode poles. Both supply lines are constructed in such a way that one cable section 7b and one coiled section 7c are attached to a cylinder section 20 made of the material in the conductive mode L4. Each two cylinder sections 20a and 20b, which are electrically connected via a coiled section 7c, thus form a "pair" which comes to rest on the electrode axis. The two cylinder sections 20a and 20b situated in a pair and the coiled section 7c connecting them come to rest on the electrode axis. In order that the cylinder sections 20a and 20b and the coiled sections 7c come to rest on the electrode axis, the cable sections 7b form a bypass, which is formed in that the cable section 7b is deflected radially outward after leaving the cylinder section 20a or 20b, to be led past the following cylinder sections 20a or 20b assigned to the other supply line, and is subsequently deflected back inward into the electrode axis, so that an electrical connection is produced to the cylinder section 20a or 20b assigned to this cable section 7b.

Figure 11B:
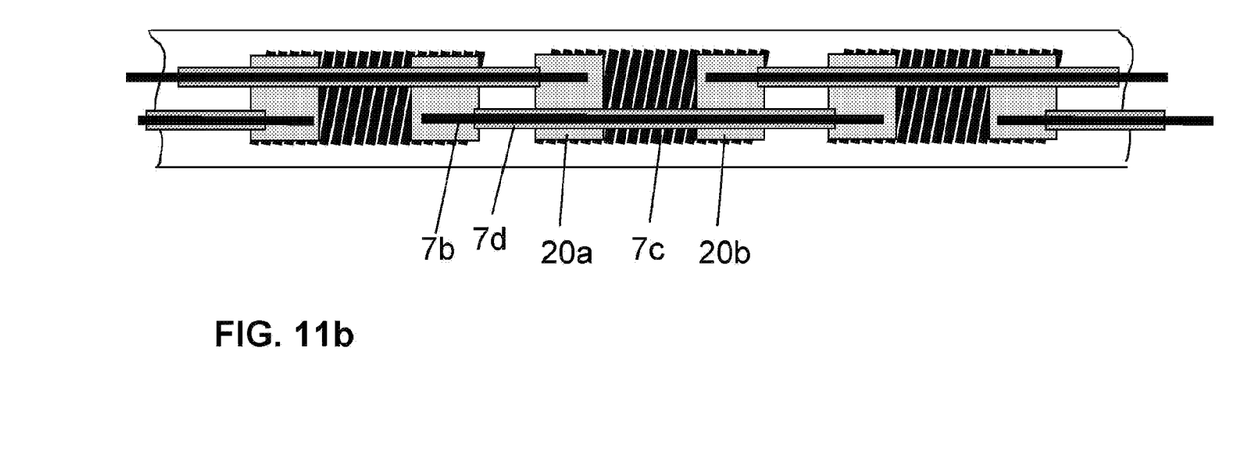

To avoid this deflection of the cable sections 7b, a construction as shown in FIG. 11b is also possible. Instead of leading the cable sections 7b past the cylinder sections 20a and 20b of the other supply line, which are connected to one another via a coiled section 7c, these sections of this cable section 7b are externally insulated by a hose 7d and led through these two cylinder sections 20a and 20b and the coiled section 7c, for example.

Figure 12A:
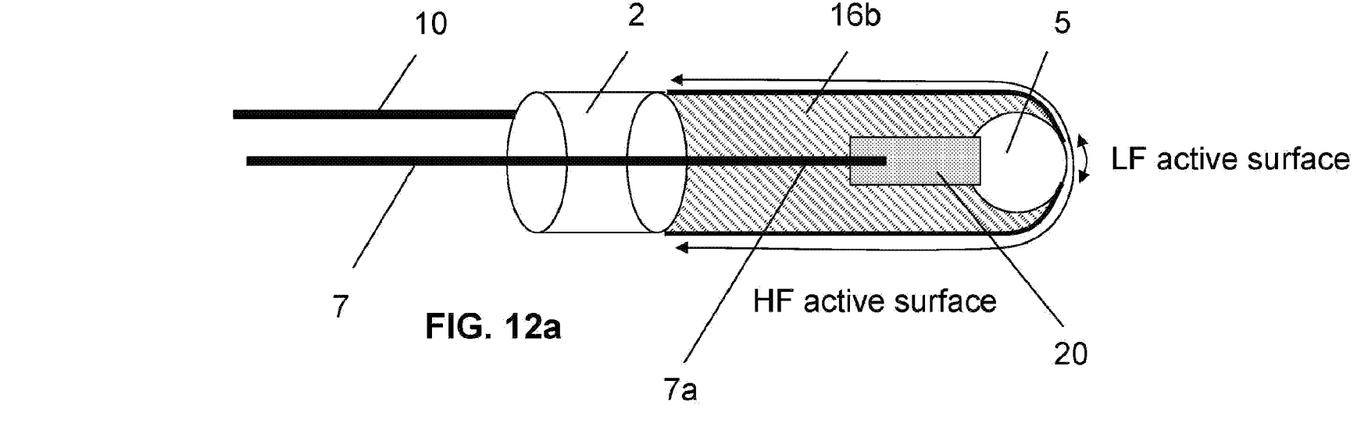

In a special embodiment, the line section implementing the line resistance R is integrated in the construction of the electrode tip. FIG. 12a shows such an embodiment. In addition, the case in which the measures according to the present invention from FIG. 8 are also implemented is shown. The material 20 having conductive mode L4 determining the line resistance R is enclosed directly by a mantle 16b made of a material having conductive mode L2. The conductivity tensor thus also changes significantly here as a function of frequency. While a low-frequency current is preferably conducted along the supply line, a high-frequency current preferably flows transversely (i.e., at a right angle to the electrode supply line), it thus does not reach or hardly reaches the electrode pole 5.

Figure 12B:
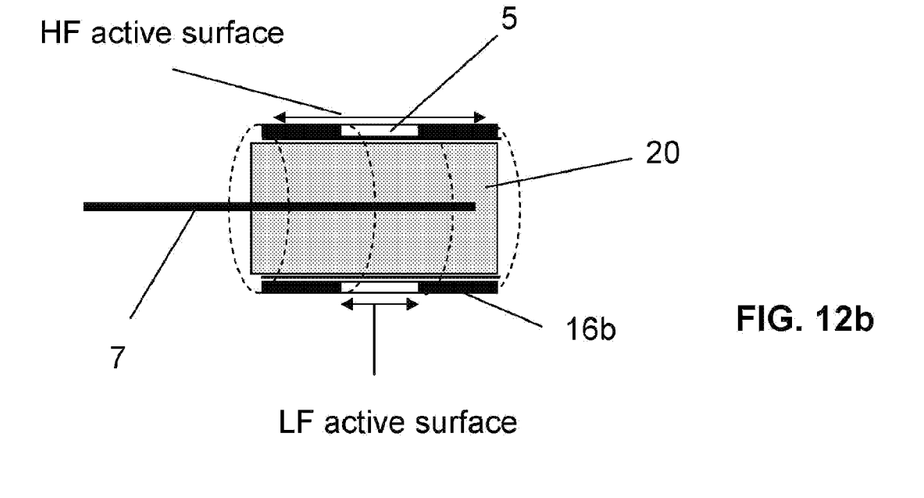

FIG. 12b shows an additional form of the construction just described for a stimulation ring electrode having an electrode pole 5. The principle is as just described. The electrode body is formed in this area by a material 20 in the conductive mode L4, which is at least partially enveloped by an electrically conductive metal layer in a suitable way. In this example, it is a layer in ring form, i.e., the electrode pole 5 is formed by this metal layer. The layer and/or the material 20 directly adjacent to the layer is partially coated by a material 16b in the conductive mode L2. The electrical supply line 7, which is made of metal or alternatively a material in the conductive mode 4, has no direct contact to the electrode pole 5. The contact occurs to the material 20 in the conductive mode L4. While a low-frequency current is conducted at low resistance from the supply line 7 to the electrode pole 5, the material 20 in the conductive mode L4 opposes high-frequency current with a greater resistance. The HF current already reduced by this increased resistance additionally not only dissipates via the electrode pole 5, but rather also via the entire surface of the material 16b. The current density is accordingly reduced further.

A further solution (not shown here) comprises integrating the line section implementing the line resistance R, made of a first material, in a typical electrode head modified in this regard, without a sheath made of a second material additionally being implemented. In a further embodiment, the sheath implemented in FIG. 12a by a second material is instead implemented by a material having lower conductivity, but having higher dielectric constants. Such a material may be produced by mixing ceramic dust into the polymer matrix (in the preferred case silicone and/or polyurethane) instead of the cited conductive particles. In a special embodiment, the particles comprise barium titanate.

What is claimed is:

1. An electrode for interventional purposes, such as a cardiac pacemaker, neurostimulation, or ICD electrode or EP catheter comprising:
    an elongate electrode body (6) having a distal end (4) and a proximal end (3) having a proximal electrode;
    at least one electrode pole (5) in an area of the distal end (4) of the elongate electrode body (6) configured to deliver an intervention pulse;
    at least one supply line (7), that is insulated within the elongate electrode body (6), and which is coupled to the at least one electrode pole (5), wherein said at least one supply line (7) comprises a first material;
    an electrode sheath (8) configured to directly contact both a body in which said elongate electrode body is implanted and said at least one supply line wherein said electrode sheath encloses the at least one supply line (7), and wherein said electrode sheath comprises a second material wherein the first and/or second material contains conductive particles embedded in a polymer matrix in a concentration which is greater than or equal to a percolation threshold,
    and wherein at least said electrode sheath is configured to degrade an antenna characteristic of said electrode as a function of changing incident frequency to limit current concentrations and excess heating at said at least one electrode pole.

2. The electrode according to claim 1, wherein the conductive particles have an elongate shape, having a length to width ratio of greater than 2.

3. The electrode according to claim 1, wherein the polymer matrix comprises silicone, polyurethane, and/or polyether block amide, and the conductive particles comprise carbon, carbon black and/or carbon fibers, carbon nanoparticles, metal-coated carbon particles, and/or carbon nanotubes, conductive soot, and/or metal particles.

4. The electrode according to claim 1, comprising multipolar electrodes having an external sheath that comprises the second material and internal sheaths for supply lines that comprise an insulation material having a resistance that does not vary based on electromagnetic frequency of an incident electromagnetic wave.

5. The electrode according to claim 1, comprising multipolar electrodes having an external sheath and one or more internal sheaths for supply lines that comprise the second material.

6. The electrode according to claim 1, wherein the first and/or second material is only implemented on sections (16a, 16b, 20, 20a, 20b) of the elongate electrode body (6) and/or the supply line (7).

7. The electrode according to claim 6, wherein the sections (16a, 16b, 20, 20a, 20b) made of the first and/or second material are located in multiple locations along said electrode so as to be distributed multiple times at specific intervals having regular or irregular distances therebetween or contacting patterns over the electrode body (6) and/or the at least one supply line (7).

8. The electrode according to claim 6, wherein the sections (16a, 16b, 20, 20a, 20b) are made of the first and/or second material and are situated at intervals (17) smaller than ¼ or less than 1/10 a wavelength of a radiated high-frequency wave typical of a magnetic resonance imaging device in the elongate electrode body (6) and/or in the at least one supply line (7).

9. The electrode according to claim 6, wherein because of a positioning of the sections (16a, 16b, 20, 20a, 20b) made of the first and/or second material and/or their contacting patterns and/or dielectric properties of their first and/or second material, intervals (17) of electrode supply line(s) (7a, 7b, 7c), which are divided by the sections (16a, 16b, 20, 20a, 20b), are tuned to one another in regard to their wave impedances so that a unidirectional reflection occurs at transitions of said sections in a direction of a proximal electrode side.

10. The electrode according to claim 1, wherein the at least one electrode pole (5) is partially covered by the second material.

11. The electrode according to claim 1, wherein electrode sheath (16b) comprising the second material extends between two electrode poles (5, 2) of a multipolar electrode.

12. The electrode according to claim 1, wherein the concentration of conductive particles in the first material of said at least one supply line (7) results in a line resistance (R) of said at least one supply line (7) that increases with increasing frequency of an incident electromagnetic wave.

13. The electrode according to claim 12, wherein the concentration of conductive particles in the first material is selected to configure a line resistance (R) with respect to frequencies of electromagnetic radiation of an incident electromagnetic wave so that for frequencies below 1000 Hz, the line resistance (R) is less than 100 ohm, and for frequencies above 20 MHz, the line resistance (R) is greater than 2 kOhm.

14. The electrode according to claim 12, wherein the concentration of conductive particles in the first material is selected to configure a line resistance (R) with respect to frequencies of electromagnetic radiation of an incident electromagnetic wave so that for frequencies below 1000 Hz, the line resistance (R) is less than 100 ohm, and for frequencies above 20 MHz, the line resistance (R) is greater than 4 kOhm.

15. The electrode according to claim 12, wherein the concentration of conductive particles in the first material is selected in such a way that for frequencies below 1000 Hz, a line resistance (R) less than 100 ohm results, and for frequencies above 20 MHz, a line resistance (R) greater than 500 ohm results.

16. The electrode according to claim 15, wherein the concentration of conductive particles in the first material is greater than 2 mass-% of total volume.

17. The electrode according to claim 1, wherein the concentration of conductive particles in the second material results in a sheath resistance (r) that decreases with increasing frequency of an incident electromagnetic wave.

18. The electrode according to claim 17, wherein the concentration of conductive particles in the second material of the electrode sheath (8) is selected along with material parameters comprising a thickness of the electrode sheath (16a, 16b) to configure a sheath resistance (r) with respect to frequencies of electromagnetic radiation of an incident electromagnetic wave so that for frequencies below 1000 Hz, the sheath resistance (r) is greater than 1 Mohm, for frequencies above 5 MHz the sheath resistance (r) is less than 10 kohm, and for frequencies above 20 MHz, the sheath resistance (r) is less than 1 kohm.

19. The electrode according to claim 18, wherein the concentration of conductive particles in the second material is between 1.25 and 20 mass-% of total volume.

20. The electrode according to claim 1, wherein the conductive particles have an elongate shape, having a length to width ratio of greater than 100.

21. The electrode according to claim 1 produced by a process comprising:
providing an electrode sheath (8) having a continuous lumen from a proximal end up to an electrode pole located at a distal end; and;
installing a supply line (7) in the continuous lumen.

22. The electrode according to claim 1, produced by a process comprising:
providing an electrode sheath (8) having a continuous lumen from a proximal end up to an electrode pole located at a distal end;
installing a supply line (7) in the continuous lumen; and,
embedding in an airtight manner of the supply line in the continuous lumen using a conductive liquid.

23. The electrode according to claim 1, wherein
the concentration of conductive particles in the first material of said at least one supply line (7) results in a line resistance (R) of said at least one supply line (7) that increases with increasing frequency of an incident electromagnetic wave; and,
the concentration of conductive particles in the second material results in a sheath resistance (r) decreases with increasing frequency of said incident electromagnetic wave.

24. An electrode for interventional purposes, such as a cardiac pacemaker, neurostimulation, or ICD electrode or EP catheter comprising:
an elongate electrode body (6) having a distal end (4) and a proximal end (3);
at least one electrode pole (5) in an area of the distal end (4) of the elongate electrode body (6) configured to deliver an intervention pulse;
at least one supply line (7), running insulated in the elongate electrode body (6), to the at least one electrode pole (5), which comprises a first material that increases in resistance as a frequency of electromagnetic radiation of an incident electromagnetic wave increases;
an electrode sheath (8) configured to directly contact both a body in which said elongate electrode body is implanted and said at least one supply line wherein said electrode sheath encloses the at least one supply line (7), and wherein said electrode sheath comprises a second material wherein the first and/or second material contains conductive particles embedded in a polymer matrix in a concentration which is greater than or equal to a percolation threshold wherein said second material decreases in resistance as the frequency of electromagnetic radiation of an incident electromagnetic wave increases and wherein at least said electrode sheath is configured to degrade an antenna characteristic of said electrode as a function of changing incident frequency to limit current concentrations and excess heating at said at least one electrode pole.

* * * * *